(12) United States Patent
Sigl et al.

(10) Patent No.: US 8,129,572 B2
(45) Date of Patent: Mar. 6, 2012

(54) PROCESS FOR CODIMERIZING OLEFINS

(75) Inventors: Marcus Sigl, Mannheim (DE); Michael Triller, Ilvesheim (DE); Thomas Heidemann, Viernheim (DE)

(73) Assignee: BASF SE, Ludwigshafen (DE)

( * ) Notice: Subject to any disclaimer, the term of this patent is extended or adjusted under 35 U.S.C. 154(b) by 464 days.

(21) Appl. No.: 12/303,527

(22) PCT Filed: Jun. 6, 2007

(86) PCT No.: PCT/EP2007/055551
§ 371 (c)(1),
(2), (4) Date: Dec. 4, 2008

(87) PCT Pub. No.: WO2007/141288
PCT Pub. Date: Dec. 13, 2007

(65) Prior Publication Data
US 2009/0312583 A1 Dec. 17, 2009

(30) Foreign Application Priority Data
Jun. 7, 2006 (EP) .................................... 06115091

(51) Int. Cl.
*C07C 29/50* (2006.01)
*C07C 2/08* (2006.01)
(52) U.S. Cl. ....................... 568/909; 585/326
(58) Field of Classification Search .................. 568/909; 585/16, 326
See application file for complete search history.

(56) References Cited

U.S. PATENT DOCUMENTS

| | | | |
|---|---|---|---|
| 3,402,217 | A | 9/1968 | Engelbrecht et al. |
| 4,029,719 | A | 6/1977 | Forni et al. |
| 5,118,901 | A | 6/1992 | Drake |
| 6,566,566 | B1 | 5/2003 | Maas et al. |
| 6,737,553 | B1 | 5/2004 | Maas et al. |
| 6,906,230 | B1 | 6/2005 | Maas et al. |
| 6,963,014 | B1 | 11/2005 | Zeller et al. |
| 2004/0220440 | A1 | 11/2004 | Dakka et al. |

FOREIGN PATENT DOCUMENTS

| | | |
|---|---|---|
| CA | 1205792 | 6/1986 |
| DE | 19859911 | 6/2000 |
| EP | 0329305 | 8/1989 |
| WO | WO-0053547 | 9/2000 |
| WO | WO-0056683 | 9/2000 |
| WO | WO-0136356 | 5/2001 |
| WO | WO-0183407 | 11/2001 |
| WO | WO-03082780 | 10/2003 |
| WO | WO-2004080935 | 9/2004 |
| WO | WO-2007040812 | 4/2007 |

OTHER PUBLICATIONS

International Preliminary Report on Patentability issued in corresponding International Application No. PCT/EP2007/055551 on Jan. 27, 2009.

*Primary Examiner* — Sikarl Witherspoon
(74) *Attorney, Agent, or Firm* — Connolly Bove Lodge & Hutz LLP

(57) ABSTRACT

The present invention relates to a process for preparing olefin codimers, the olefin codimers which can be obtained by this process, a process for preparing alcohols in which such olefin codimers are subjected to hydroformylation and subsequent hydrogenation, the alcohol mixtures which can be obtained in this way and their use.

17 Claims, No Drawings

PROCESS FOR CODIMERIZING OLEFINS

CROSS REFERENCE TO RELATED APPLICATIONS

This application is a national phase of PCT/EP2007/055551, filed on Jun. 6, 2007 which claims priority to EP 06115091.8 filed Jun. 7, 2006, the entire contents of all are hereby incorporated by reference.

The present invention relates to a process for preparing olefin codimers having from 6 to 18 carbon atoms, the olefin codimers which can be obtained by this process, a process for preparing alcohols in which such olefin codimers are subjected to hydroformylation and subsequent hydrogenation, the alcohol mixtures which can be obtained in this way and their use.

Hydrocarbon mixtures comprising short-chain olefins, e.g. olefins having from 2 to 6 carbon atoms, are obtainable on an industrial scale. Thus, for example, a hydrocarbon mixture which is referred to as $C_4$ fraction and has a high total olefin content, with the olefins being essentially ones having 4 carbon atoms, is obtained in the processing of petroleum by steam cracking or fluid catalytic cracking (FCC). Such $C_4$ fractions, i.e. mixtures of isomeric butenes and butanes, are very well suited, if appropriate after prior removal of the isobutene and hydrogenation of the butadiene comprised, to the preparation of oligomers, in particular octenes and dodecenes.

The essentially linear oligomer mixtures obtainable from olefin mixtures comprising predominantly linear starting olefins have attained great importance. They are suitable, for example, as diesel fuel component and as intermediates for the preparation of functionalized, predominantly linear hydrocarbons. Thus, hydroformylation and subsequent hydrogenation of the olefin oligomers gives the corresponding alcohols which are used, inter alia, as starting materials for detergents and as plasticizers.

It is known that fatty alcohols having from about 8 to 20 carbon atoms can be used for preparing nonionic and anionic surfactants. For this purpose, the alcohols are subjected to an appropriate functionalization, e.g. by alkoxylation or glycosidation. The alkoxylates obtained can either be used directly as nonionic surface-active substances or be converted into anionic surface-active substances by further functionalization, e.g. by sulfation or phosphation. The use properties of these surfactants, e.g. their wetting capability, foam formation, fat dissolution capability, biodegradability, etc., are determined essentially by the chain length and the degree of branching of the hydrophobic hydrocarbon radical of the alcohol used. Alcohols which are well suited to further processing to give effective surfactants are also referred to as surfactant alcohols.

The degree of branching of the olefins plays a critical role for use as surfactant alcohols. The degree of branching is described, for example, by the ISO index which indicates the mean number of methyl branches of the respective olefin fraction. Thus, for example, in a $C_{12}$ fraction, the n-dodecenes contribute 0, methylundecenes contribute 1 and dimethyldecenes contribute 2 to the ISO index of the fraction. The lower the ISO index, the greater the linearity of the molecules in the respective fraction.

The use of heterogeneous catalysts comprising predominantly nickel as active components for preparing slightly branched oligomers from lower olefins is known.

In the DIMERSOL process (cf. Revue de l'Institut Français du Petrole, Vol. 37, No. 5, September/October 1982, p. 639ff), propene or butene is oligomerized in a homogenous phase in the presence of a catalyst system comprising a transition metal derivative and an organometallic compound. Typical catalyst systems are Ni(O) complexes in combination with Lewis acids such as $AlCl_3$, $BF_3$, $SbF_5$ etc., or Ni(II) complexes in combination with alkylaluminum halides.

Heterogeneous catalysts have the advantage over homogeneous catalysts that it is not necessary to separate the catalyst from the discharge from the reactor. Furthermore, the catalyst costs per metric ton of product are generally higher in the homogeneously catalyzed process than in a heterogeneously catalyzed process.

Processes for oligomerizing olefins over nickel-comprising heterogeneous catalysts for the preparation of surfactant alcohols are described, for example, in WO 00/53547, DE-A-198 59 911 and WO 00/56683.

WO 01/36356 describes a process for preparing a $C_{13}$ alcohol mixture, which comprises
a) bringing a butene-comprising $C_4$-hydrocarbon stream which comprises less than 5% by weight, based on the butene fraction, of isobutene into contact with a nickel-comprising heterogeneous catalyst at elevated temperature,
b) isolating a $C_{12}$-olefin fraction from the reaction mixture,
c) hydroformylating the $C_{12}$-olefin fraction by reaction with carbon monoxide and hydrogen in the presence of a cobalt catalyst and
d) hydrogenating the hydroformylation product.

The $C_{12}$-olefin fraction has an ISO index of from 1.9 to 2.3. This document also describes the use of the $C_{13}$-alcohol mixtures as surfactant alcohols.

The use of nickel-comprising catalysts based on zeolites of the Faujasite type for the oligomerization of olefins is known. Such catalysts are described in U.S. Pat. No. 3,402,217 and EP-A-0 329 305. It is also known that these nickel-comprising zeolites can be subjected to a modification in order to increase the proportion of slightly branched or linear olefins in the olefin mixture obtained in the oligomerization. Such a modification can be, for example, doping of the zeolites with Ca, Cd, Zn or Mn ions.

U.S. Pat. No. 4,029,719 describes a process for preparing linear olefins by oligomerization of $C_3$-$C_{12}$-olefins using a zeolitic catalyst which has been laden with metals of transition group VIII by ion exchange and treated with an organic or inorganic base to activate it.

CA 1,205,792 describes a catalyst for olefin dimerization which has been obtained by depositing nickel on a zeolite and subsequently bringing it into contact with an amine.

US 2004/0220440 A1 describes a process for oligomerizing olefinic hydrocarbon streams comprising sulfur-comprising impurities, in which the hydrocarbon starting material is firstly brought into contact with a first metal oxide catalyst to convert the sulfur compounds which act as catalyst poison into unproblematical compounds and then with a second olefin oligomerization catalyst. The first metal oxide catalyst used is preferably a nickel-comprising catalyst. Many different zeolites are mentioned as possible second olefin oligomerization catalyst. As regards the olefin starting material, it is stated quite generally and without the support of an example that it can also consist of an oligomer or comprise such an oligomer, e.g. from the recirculation of part of the product stream. The examples are restricted to the oligomerization of propene-rich $C_3$ streams which have previously been brought into contact with a nickel-comprising catalyst to convert the sulfur compounds comprised.

WO 2004/080935 describes a process for dimerizing lower olefinic hydrocarbons, in which an olefin feed is brought into contact with an acid catalyst based on a natural or synthetic zeolite of intermediate pore size in a reaction zone, a stream comprising dimerized olefins is taken from the reaction zone, a stream comprising dimerization products and a stream comprising unreacted hydrocarbons are separated off from the discharge from the reaction zone and the stream comprising unreacted hydrocarbons is at least partly recirculated to the reaction zone. The dimerization of mixtures of olefins having different numbers of carbon atoms or a partial recirculation of dimerization product is not taught.

If olefin mixtures comprising olefins having different numbers of carbon atoms are used for the oligomerization, the more reactive relatively short-chain olefins generally react preferentially with dimerization to form the homodimer. In a batch process, the reaction mixture can then become severely depleted in the relatively short-chain olefin through to complete reaction of the relatively short-chain olefin to form the homodimer before the longer-chain olefin is also subjected to oligomerization. Depending on the reactivity of the relatively long-chain olefin and of the homodimers or homo-oligomers of the relatively short-chain olefin, homodimers of the relatively long-chain olefin or other oligomerization products, e.g. cooligomers from the reaction of the relatively long-chain olefin with homodimers of the relatively short-chain olefin, are then preferentially formed. In a continuous process, there can, in an extreme case, be exclusive formation of homodimers of the relatively short-chain olefin while the unreacted relatively long-chain olefin is essentially completely recovered in the reaction discharge. In addition, cooligomerization products have in the past frequently been regarded as undesirable by-products of olefin oligomerization.

It has now surprisingly been found that oligomerization of olefin mixtures to give the cooligomerization product in good yield and selectivity is possible when using heterogeneous olefin oligomerization catalysts. This applies in particular to oligomerization of olefin mixtures which comprise $C_n$-olefins and $C_{2n}$-olefins, with it being possible to obtain the $C_{3n}$-cooligomerization product in good yield and selectivity. Furthermore, it has surprisingly been found that specific heterogeneous olefin oligomerization catalysts based on sheet silicates and/or framework silicates are suitable for these cooligomerizations. It has also surprisingly been found that the $C_{m+n}$-cooligomerization products and especially the $C_{3n}$-cooligomerization products obtainable by this process have particularly advantageous use properties, in particular in further processing to produce surfactant alcohols.

The invention accordingly provides a process for codimerizing olefins, which comprises
a) providing a first olefin starting material which consists essentially of $C_n$-olefins and providing a second olefin starting material which consists essentially of $C_m$-olefins, where n and m are, independently of one another, two different integers from 2 to 12, and
b) reacting the first and second olefin starting materials over a heterogeneous olefin oligomerization catalyst.

For the purposes of the present invention, the term "dimers" refers to the products of combining two olefin molecules to form one molecule whose number of carbon atoms corresponds to the sum of the carbon atoms of the two combined olefins. The dimers are themselves olefinically unsaturated. "Homodimers" are dimers from combining two identical olefins. If at least one of the olefin starting materials comprises a mixture of olefins having the same number of carbon atoms, the term "homodimers" refers to dimers from combining two olefins having the same number of carbon atoms. "Codimers" are dimers from combining olefins having different numbers of carbon atoms. If at least one of the olefin starting materials comprises a mixture of olefins having the same number of carbon atoms, the codimers are generally also obtained in the form of a codimer mixture.

The process of the invention makes it possible to prepare an olefin oligomerization product from a first olefin starting material which comprises at least one $C_m$-olefin and a second olefin starting material which comprises at least one $C_n$-olefin, with the reaction product comprising a substantial proportion of codimers of $C_m$-olefins and $C_n$-olefins (i.e. $C_{n+m}$-olefins). For the purposes of the present invention, a "substantial proportion" is a proportion of at least 5% by weight, particularly preferably at least 10% by weight, in particular at least 12% by weight, based on the total amount of the olefins comprised in the reaction discharge (unreacted olefins, homodimers, codimers and other oligomerization products).

The olefin oligomerization catalysts used according to the invention make olefin codimerization possible. The codimer content of the reaction product can be controlled not only by means of the catalyst used (and also further operating parameters such as the pressure and the temperature in the oligomerization and the residence time) but also by means of the ratio of $C_m$-olefin to $C_n$-olefin fed in and, if present, material to be recirculated from the reaction product. Further important reaction parameters are the residence time and the conversion.

In a preferred embodiment, a first olefin starting material which comprises at least one olefin having from two to six carbon atoms ($C_n$-olefin) and a second olefin starting material which comprises at least one olefin having twice as many carbon atoms as the first olefin starting material ($C_{2n}$-olefin) is provided in step a). The reaction product then comprises a substantial proportion of codimers of $C_n$-olefins and $C_{2n}$-olefins (i.e. $C_{3n}$-olefins).

In the olefin starting materials provided in step a), n is preferably 4, 5 or 6, in particular 4. In the olefin starting materials provided in step a), m is preferably from 6 to 10, in particular 8.

Preferred first olefin starting materials for step a) are in principle all compounds which comprise from 2 to 6 carbon atoms and at least one ethylenically unsaturated double bond. Preference is given to first olefin starting materials which comprise olefins having from 4 to 6 carbon atoms, in particular 4 carbon atoms. The olefins used for the oligomerization are preferably selected from among linear (straightchain) olefins and olefin mixtures which comprise at least one linear olefin. These include ethene, propene, 1-butene, 2-butene, 1-pentene, 2-pentene, 1-hexene, 2-hexene, 3-hexene and mixtures thereof.

The first olefin starting material preferably has a proportion of olefins having the same number of carbon atoms of at least 70% by weight, particularly preferably at least 90% by weight, in particular 95% by weight and especially at least 99% by weight, based on the total olefin content.

The first olefin starting material preferably has a proportion of linear olefins of at least 30% by weight, particularly preferably at least 40% by weight, in particular at least 50% by weight, based on the total olefin content.

In a specific embodiment, use is made of a first olefin starting material which has a proportion of branched olefins of not more than 20% by weight, particularly preferably not more than 10% by weight, in particular not more than 5% by weight, especially not more than 3% by weight, based on the total olefin content.

Preference is given to using an industrially available olefin-comprising hydrocarbon mixture as first olefin starting material in step a) of the oligomerization process of the invention.

Preferred industrially available olefin mixtures result from hydrocarbon cracking in petroleum processing, for example by catalytic cracking such as fluid catalytic cracking (FCC), thermal cracking or hydrocracking with subsequent dehydrogenation. A suitable industrial first olefin mixture is the $C_4$ fraction. $C_4$ fractions can be obtained, for example, by means of fluid catalytic cracking or steam cracking of gas oil or by steam cracking of naphtha. Depending on the composition of the $C_4$ fraction, a distinction is made between the total $C_4$ fraction (crude $C_4$ fraction), the raffinate I obtained after 1,3-butadiene has been separated off and the raffinate II obtained after the isobutene has been separated off. A further suitable industrial first olefin mixture is the $C_5$ fraction obtainable in naphtha cracking. Olefin-comprising hydrocarbon mixtures having from 4 to 6 carbon atoms which are suitable for use in step a) can also be obtained by catalytic dehydrogenation of suitable industrially available paraffin mixtures. Thus, for example, $C_4$-olefin mixtures can be produced from liquefied petroleum gas (LPG) and liquefied natural gas (LNG). The latter comprise not only the LPG fraction but also additionally relatively large amounts of relatively high molecular weight hydrocarbons (light naphtha) and are thus also suitable for producing $C_5$- and $C_6$-olefin mixtures. Olefin-comprising hydrocarbon mixtures comprising monoolefins having from 4 to 6 carbon atoms are produced from LPG or LNG streams by the customary processes known to those skilled in the art, which generally comprise not only dehydrogenation but also one or more work-up steps. These include, for example, the removal of at least part of the saturated hydrocarbons comprised in the abovementioned olefin starting mixtures. These can, for example, be reused for producing olefin starting materials by cracking and/or dehydrogenation. However, the olefins used in the process of the invention can also comprise a proportion of saturated hydrocarbons which are inert under the oligomerization conditions according to the invention. The proportion of these saturated components is generally not more than 60% by weight, preferably not more than 40% by weight, particularly preferably not more than 20% by weight, based on the total amount of olefins and saturated hydrocarbons comprised in the hydrocarbon starting material.

A raffinate II suitable for use in the process of the invention has, for example, the following composition:
from 0.5 to 5% by weight of isobutane,
from 5 to 30% by weight of n-butane,
from 20 to 40% by weight of trans-2-butene,
from 10 to 20% by weight of cis-2-butene,
from 25 to 55% by weight of 1-butene,
from 0.5 to 5% by weight of isobutene
and also trace gases such as 1,3-butadiene, propene, propane, cyclopropane, propadiene, methylcyclopropane, vinylacetylene, pentenes, pentanes, etc., in the range up to a maximum of 1% by weight each.

A suitable raffinate II has the following typical composition:

| | |
|---|---|
| Butanes | 26% by weight |
| i-Butene | 1% by weight |
| 1-Butene | 26% by weight |
| trans-2-Butene | 31% by weight |
| cis-2-Butene | 16% by weight |

If diolefins or alkynes are present in the first olefin-rich hydrocarbon mixture, these can be removed from the mixture to preferably less than 200 ppm by weight before the oligomerization. They are preferably removed by selective hydrogenation, e.g. as described in EP-81 041 and DE-15 68 542, particularly preferably by selective hydrogenation down to a residual content of less than 100 ppm by weight, in particular 10 ppm by weight.

In addition, oxygen-comprising compounds such as alcohols, aldehydes, ketones or ethers are advantageously mostly removed from the olefin-rich hydrocarbon mixture. For this purpose, the olefin-rich hydrocarbon mixture can advantageously be passed over an adsorbent such as a molecular sieve, preferably an adsorbent as described in DE-A-19845857, which is hereby incorporated by reference. The concentration of oxygen-comprising, sulfur-comprising, nitrogen-comprising and halogen-comprising compounds in the olefin-rich hydrocarbon mixture is preferably less than 20 ppm by weight, particularly preferably less than 10 ppm by weight, in particular less than 1 ppm by weight.

Preferred second olefin starting materials for step a) are in principle all compounds which have from 4 to 12 carbon atoms and an ethylenically unsaturated double bond. Preference is given to second olefin starting materials which comprise olefins having from 8 to 12 carbon atoms, in particular olefins having 8 carbon atoms. The olefins used for the oligomerization are preferably selected from among linear and slightly branched olefins and olefin mixtures.

Suitable octenes are, for example. 1-octene, 2-octene, 3-octene, 4-octene, 2-methyl-hept-1-ene, 2-methylhept-2-ene, 2-methylhept-ene, 6-methylhept-3-ene, 6-methyl-hept-2-ene, 6-methylhept-1-ene, 3-methylhept-1-ene, 3-methyl-hept-2-ene, 3-methyl-hept-3-ene, 5-methylhept-3-ene, 5-methylhept-2-ene, 5-methylhept-1-ene, 4-methyl-hept-1-ene, 4-methylhept-2-ene, 4-methylhept-3-ene and mixtures thereof.

The second olefin starting material preferably has a proportion of olefins having the same number of carbon atoms of at least 70% by weight, particularly preferably at least 90% by weight, in particular at least 95% by weight, especially at least 99% by weight.

The second olefin starting material preferably has a degree of branching of the olefins, determined as the ISO index, in the range from 0 to 1.8, particularly preferably from 0.5 to 1.5, in particular from 0.8 to 1.3.

Preference is given to using an industrially available second olefin starting material in step a) of the oligomerization process of the invention.

Preferred industrially available $C_8$-olefin mixtures are obtained, for example, in the DIMERSOL process in which butene is oligomerized in a homogeneous phase in the presence of a catalyst system comprising a transition metal derivative and an organometallic compound (Revue de l'Institut Français du Petrole, Vol. 37, No. 5, September/October 1982, p. 639ff). $C_8$-olefin mixtures suitable as second olefin starting material also result from the Octol process of Hüls AG (Hydrocarbon Processing, February 1992, p. 45/46). Suitable processes for preparing slightly branched $C_8$-olefin mixtures are also described in DE-A43 39 713 and WO 99/25668, which are hereby fully incorporated by reference. In a preferred embodiment, the second olefin starting material is obtained by dimerization of a raffinate II, as defined above, in the presence of a nickel-comprising oligomerization catalyst.

The reaction of the olefin starting materials in step b) is preferably carried out continuously.

For this purpose, the first olefin starting material and the second olefin starting material are fed into a reactor system and reacted over an olefin oligomerization catalyst.

In a specific embodiment, the reaction product from step b) is separated into a first substream and a second substream, the first substream is subjected to a work-up to give a fraction comprising essentially the codimerization product and the second substream is recirculated to step a). This recirculated feed stream consists essentially of oligomers, unreacted olefins and possibly saturated hydrocarbons.

In a specific embodiment, an olefin-comprising stream obtained in the work-up of the reaction product from step b) or of the first substream of the reaction product from step b) is additionally fed into the reaction system.

The molar ratio of $C_m$-olefins to $C_n$-olefins, in particular the molar ratio of $C_{2n}$-Olefins to $C_n$-olefins, based on the total amount of olefins fed in, is preferably in the range from 0.25:1 to 4:1, particularly preferably in the range from 0.5:1 to 3:1, in particular in the range from 1:1 to 2.5:1.

The reaction system used in step b) of the process of the invention can comprise one or more, identical or different reactors. In the simplest case, the reaction system is formed by a single reactor. If a plurality of reactors is used, these can in each case have identical or different mixing characteristics. The individual reactors can, if desired, be divided one or more times by means of internals. If two or more reactors form the reaction system, these can be connected to one another in any way, e.g. in parallel or in series. In a preferred embodiment, a reaction system comprising two reactors connected in series is used.

Suitable pressure-rated reaction apparatuses for the oligomerization are known to those skilled in the art. These include the generally customary reactors for gas-solid and gas-liquid reactions, e.g. tube reactors, stirred vessels, gas recycle reactors, bubble columns, etc., which may, if appropriate, be divided by internals. Preference is given to using shell-and-tube reactors or shaft furnaces. The catalyst can be present in a single fixed catalyst bed or in a plurality of fixed catalyst beds in the reactor or reactors. It is possible to use different catalysts in the individual reaction zones. However, the use of the same catalyst in all reaction zones is preferred.

The temperature in the oligomerization reaction is generally in the range from about 20 to 280° C., preferably from 25 to 200° C., in particular from 30 to 140° C. If the reaction system comprises more than one reactor, these reactors can have identical or different temperatures. Likewise, a reactor can have a plurality of reaction zones which can be operated at various temperatures. Thus, for example, the temperature in a second reaction zone of an individual reactor can be set so as to be higher than that in the first reaction zone, or a higher temperature can be set in the second reactor of a reactor cascade than in the first reactor, e.g. to achieve a conversion as complete as possible.

The pressure in the oligomerization is generally in the range from about 1 to 300 bar, preferably from 5 to 100 bar and in particular from 10 to 70 bar. When a plurality of reactors is used, the reaction pressure in the individual reactors can be different.

In a specific embodiment, the temperatures and pressures used for the oligomerization are selected so that the olefin-comprising starting material is liquid or in the supercritical state.

The reaction in step b) is preferably not carried out adiabatically (but instead preferably with removal of the heat of reaction by heat exchange with an external heat transfer medium). Suitable apparatuses for heat exchange and for removing process heat are the customary ones known to those skilled in the art. The heat exchange apparatus can be installed on or in the reactor. In the above-described process variant with recirculation of a second substream of the reaction product, heat is taken from the substream by bringing it into contact with an external heat transfer medium. The quantity of heat recovered can be reused at another point in the process, e.g. in the fractionation of the reaction product.

If desired, the reaction in step b) can also be carried out adiabatically. For the purposes of the present invention, this term is used in the industrial sense and not in the physicochemical sense. Thus, the oligomerization reaction generally proceeds exothermically, so that the reaction mixture experiences an increase in temperature on flowing through the reaction system, for example a catalyst bed. An adiabatic reaction is understand to mean a procedure in which the quantity of heat liberated in an exothermic reaction is taken up by the reaction mixture in the reactor and no cooling by means of cooling devices is employed. Thus, the heat of reaction is removed from the reactor together with the reaction mixture, apart from a residual proportion which is given off from the reactor to the environment by means of natural thermal conduction and thermal radiation.

The olefin oligomerization catalyst used in step b) preferably comprises at least one silicate selected from among sheet silicates, framework silicates and combinations thereof.

The olefin oligomerization catalyst used in step b) in accordance with the invention comprises essentially no nickel. For the purposes of the invention, this is a catalyst having a nickel content, based on elemental nickel, of not more than 1% by weight, particularly preferably not more than 0.1% by weight, in particular not more than 0.01% by weight, based on the total weight of the catalyst.

It has been found that olefin oligomerization catalysts having a high crystallinity of the silicates comprised as active component in them have particularly advantageous properties in the cooligomerization of olefin streams. For the purposes of the invention, the individual atoms of the crystalline sheet silicates or framework silicates have a regular long-range order in a lattice structure. Crystalline silicates have characteristic line positions in the X-ray diffraction pattern (XRD). The proportion of crystalline material can be determined quantitatively via the intensity of the reflections or their width. The sheet and/or framework silicates of the oligomerization catalyst used in step b) preferably have a proportion of crystalline material of at least 50% by weight, particularly preferably at least 75% by weight.

The olefin oligomerization catalyst used in step b) preferably comprises at least one microporous or mesoporous silicate. According to IUPAC, microporous solids are solids having a mean pore radius of less than 2 nm. Mesoporous solids are solids having a mean pore radius in the range from 2 to 50 nm.

Preferred sheet silicates are the clay minerals. These include, for example, two-layer, three-layer and four-layer clay minerals which differ in terms of the sequence of their tetrahedral and octahedral layers. Suitable clay minerals are, for example, aluminum silicates which are made up of layers of $SiO_2$ tetrahedra and layers of $Al_2O_3$ octahedra, with part of the silicon in the layer of tetrahedra being able to be replaced by trivalent cations, preferably aluminum, and/or part of the aluminum in the layer of octahedra being able to be replaced by divalent cations, e.g. magnesium.

The olefin oligomerization catalyst is then preferably selected from among bentonite, kaolinite, montmorilonite, attapulgite, hectorite, sepiolite, pillared clays and combinations thereof.

The preparation of "pillared clays" is comprehensively described in, for example, Figuras, Catal. Rev. Sci. Eng., 30(3) (1988), pages 457 to 499, or Jones, Catal. Today (2 (1988) 357. These documents are hereby incorporated by reference. Pillared clays are especially suitable for producing acidic oligomerization catalysts, since sheet silicates comprising protons instead of alkali metal or alkaline earth metal ions are generally less temperature-stable and in the pillared clays the individual layers are supported by one another.

Pillared clays (PILCs) are made up of layers such as montmorillonite, beidellite, hectorite or saponite, between which oxides are intercalated in the form of pillars. The pillars can, for example, be obtained by ion exchange of the layer compound with voluminous cations such as $[Al_{13}O_4(OH)_{24}(H_2O)_{12}]^{7+}$ or $[Zr_4(OH)_8(H_2O)_{16}]^{8+}$ followed by calcination. The latter leads to formation of $Al_2O_3$ or $ZrO_2$ pillars for the cations mentioned. Other oxides which can be intercalated are, for example, $TiO_2$, $Cr_2O_3$, $SiO_2$, $Ta_2O_5$, $Fe_2O_3$, mixtures thereof or mixtures with other metal oxides such as MgO. Sulfides such as $Fe_2S_3$ can also serve as pillars instead of the oxides or in addition to these. The space opened up between the layer structures by means of the pillars is available as pore volume for the reactants. Additional pore volume can be created by delamination.

The pillared clays can, like the other oligomerization catalysts based on silicate, be subjected to shaping. For this purpose, the pillared clays can be used as such or in combination with at least one auxiliary as defined below. Suitable binders for pillared clays are various aluminum oxides, preferably boehmite, amorphous aluminosilicates, e.g. ones having an $SiO_2/Al_2O_3$ ratio of from 25:75 to 95:5, silicon dioxide, preferably finely divided $SiO_2$, mixtures of finely divided $SiO_2$ and finely divided $Al_2O_3$, finely divided $TiO_2$, $ZrO_2$ and also clays.

The olefin oligomerization catalyst used in step b) preferably comprises at least one zeolite or consists of at least one zeolite.

Zeolites suitable as starting material for the catalysts used according to the invention are in principle the crystalline, naturally occurring or synthetic framework silicates known under this name. They can vary in terms of their composition, but generally comprise not only silicon, aluminum and oxygen but also at least one alkali metal and/or alkaline earth metal. If desired, the aluminum in the zeolites can be replaced partly or completely by one or more atoms which are different therefrom. The atoms which are different from aluminum are preferably selected from among B, Ga, Fe, Si and Ti.

In the process of the invention, preference is given to using zeolites having a mean pore diameter of at least 5 Å, particularly preferably at least 6 Å, in particular at least 7 Å.

Preferred zeolites are selected from among the following structure types: BEA, MFI, MEL, FAU, MOR, MWW, LTL, LTA, CHA, TON, MTW, FER, MAZ, EPI and GME. Particularly preferred zeolites are selected from among the following structure types: BEA, MFI, MEL, FAU, MOR, MWW, FER.

The silicates used according to the invention as or in the olefin oligomerization catalysts, especially zeolites, can be used, for example, in the $H^+$, ammonium, alkali metal or alkaline earth metal form.

The silicates used according to the invention, especially zeolites, can be subjected to at least one modification step before they are used for the olefin oligomerization. Such modification steps include, for example, modification with acids, ammonium salt solutions and/or metal salt solutions. They also include dealumination of the aluminum incorporated in the silicate framework, dehydroxylation, extraction of "extra-framework" aluminum oxide or silylation. Furthermore, the olefin oligomerization catalyst can be modified by subjecting it to shaping, thermal treatment or treatment with steam (steaming). Such a modification makes it possible to achieve a very high selectivity, high conversions, long catalyst operating times and/or a large number of possible regeneration cycles.

In a preferred embodiment, modification of the silicates used according to the invention can be effected by intimate contacting with aqueous salt solutions comprising ammonium salts, salts of alkali metals such as Na and K, alkaline earth metals such as Ca, Mg, earth metals such as Tl, transition metals such as Ti, Zr, Mn, Fe, Mo, Cu, Zn, Cr, noble metals or rare earth metals such as La, Ce or Y or mixtures thereof. This generally results in at least partial ion exchange of cations of the silicate, especially the zeolite, by other cations from the salt solution. The contacting with the salt solution is preferably carried out so that the silicate is completely surrounded by salt solution. Methods which are suitable for this purpose are, for example, the customary dipping and impregnation processes as are known for catalyst production. During the treatment of the silicate, the salt solution is preferably moved past the silicate, e.g. by means of stirring or pumped circulation.

In a preferred embodiment, an acidic olefin oligomerization catalyst is used in step b) of the process of the invention. Suitable silicates having acid sites can comprise Lewis and/or Brönsted acids. These silicates can be either naturally occurring acidic silicates or silicates which have been modified to make them acidic by bringing them into contact with at least one Lewis and/or Brönsted acid. Sheet silicates having negative charges occur in nature, e.g. in the form of montmorillonites, vermiculites or hectorites. Further details regarding acid sheet silicates may be found in Z. M. Thomas and W. Z. Thomas, Principles and Practice of Heterogeneous Catalysis, 1997, Vetc. ISBN 3-527-29239-8, p. 347 ff.

In a preferred embodiment, modification of the silicates used according to the invention can be effected by intimate contacting with Lewis or Brönsted acids, preferably with protonic acids and in particular with aqueous solutions of at least one protonic acid. This generally results in partial or complete balancing of the negative charges in the silicates by protons due to partial or complete replacement of the exchangeable cations comprised, in general alkali metal or alkaline earth metal ions, by protons. This is achieved in a known manner, e.g. by treatment with nitric acid or hydrochloric acid or by treatment with ammonium salts and subsequent driving-off of ammonia by calcination.

In a preferred embodiment of the process of the invention, a zeolite in the $H^+$ form is used as olefin oligomerization catalyst in step b).

The silicates to be used according to the invention can be applied to a support and/or be subjected to shaping.

As support material for the catalysts used according to the invention, it is possible to use virtually all support materials of the prior art as are advantageously used in the production of supported catalysts, for example $SiO_2$ (silica), porcelain, magnesium oxide, tin dioxide, silicon carbide, rutile, $Al_2O_3$ (alumina), clays, aluminum silicate, steatite (magnesium silicate), $ZrO_2$, zirconium silicate, cerium silicate, cellulose materials, polymers, metals, graphite or combinations of at least two of these support materials. It is also possible to use the catalysts on glass or other bodies such as woven meshes (in particular metal meshes) of any type, especially in the form of monoliths.

The olefin oligomerization catalysts can be used in the form of a powder. The olefin oligomerization catalysts are preferably used in particulate form. The catalyst particles generally have a mean of the (largest) diameter of from 0.5 to 20 mm, preferably from 1 to 10 mm. These include, for example, catalysts in the form of granules or crushed material, e.g. having a particle diameter of preferably from 0.5 to 5 mm, in particular from 0.5 to 2 mm, pellets, e.g. having a diameter of from 2 to 6 mm and a height of from 3 to 5 mm, rings having, for example, an external diameter of from 5 to 7 mm, a height of from 2 to 5 mm and a hole diameter of from 2 to 3 mm, or extrudates of various lengths having a diameter of, for example, from 1.0 to 5 mm. Such shapes can also be obtained in a manner known per se by tableting, ram extrusion or extrusion. To produce granules or crushed material, larger shaped bodies can be broken up. These granules or this crushed material and also the other shaped catalyst bodies mentioned preferably comprise virtually no material finer than 0.5 mm minimum particle diameter.

Customary auxiliaries can be added to the silicate composition for shaping by tableting, ram extrusion or extrusion. These include lubricants, binders, shaping aids and/or reinforcing materials. Suitable lubricants are, for example, graphite, polyethylene oxide, cellulose or fatty acids (such as stearic acid). Suitable binders, shaping aids and reinforcing materials are, for example, selected from among aluminum oxides, preferably boehmite, titanium dioxide, the various silicates used as catalytically active composition and fibers composed of glass, asbestos or silicon carbide. Preferred binders are amorphous aluminosilicates, silicon dioxide, preferably finely divided silicon dioxide such as silica sols, mixtures of finely divided silicon dioxide and finely divided aluminum oxide, finely divided titanium dioxide and clays. If binders and/or other auxiliaries are used, extrusion or tableting is advantageously preceded by a mixing or kneading process.

If appropriate, a calcination step is carried out after a chemical modification and/or supporting/shaping step.

If the catalyst has been subjected to wet-chemical modification, it can be additionally subjected to drying before calcination. The temperature during drying is preferably from 40 to 180° C., particularly preferably from 80 to 150° C. Drying can be carried out in apparatuses customary for this purpose, e.g. belt dryers, drying ovens and drying chambers. A gas stream (e.g. a stream of air) can additionally be conveyed past the particles during drying.

Calcination is preferably carried out at a temperature in the range from about 200 to 600° C., particularly preferably from 300 to 550° C. Calcination is preferably carried out in a gas stream, in general a stream of air. The amount of gas used in the calcination (based on the amount of catalyst and the time) is, for example in the range from about 100 to 2000 l/l×h. The duration of the calcination is preferably at least 30 minutes, particularly preferably at least one hour. In general, a calcination time of not more than 24 hours, particularly preferably not more than 12 hours, is sufficient. In addition to the calcination, the catalyst according to the invention can be subjected to activation before being used for the oligomerization of olefins. The activation is preferably carried out at a temperature in the range from about 150 to 400° C., particularly preferably from 200 to 300° C. Activation is preferably carried out in a gas stream, particularly preferably in the presence of oxygen-depleted air or an inert gas. The amount of gas used for the activation is preferably in the range from about 100 to 2000 l/l×h. The activation time is preferably at least 30 minutes, particularly preferably at least one hour. In general, an activation time of not more than 24 hours, particularly preferably not more than 12 hours, is sufficient.

Treatment with steam enables the type and proportion of the oligomerization products obtained to be optimized. This applies particularly to catalysts based on acidic silicates, especially acidic zeolites.

The catalysts according to the invention preferably comprise from 10 to 100% by weight, particularly preferably from 20 to 95% by weight, in particular from 30 to 80% by weight, of active silicate composition, based on their total weight.

The above-described catalysts display a higher activity and/or selectivity in relation to the formation of codimers than do corresponding catalysts of the prior art which are based on nickel, especially nickel oxide.

The reaction product taken off in step b) preferably has a content of codimers ($C_{m+n}$-olefins or $C_{3n}$-olefins) of at least 5% by weight, particularly preferably at least 10% by weight, in particular at least 12% by weight, based on the total weight of the reaction product taken off.

The reaction product taken off in step b) preferably has a ratio of homodimers of the higher olefin (in the specific embodiment, $C_{4n}$-olefins, i.e. homodimers of the $C_{2n}$-olefin) to codimers (especially $C_{3n}$-Olefins) of $1:\geqq 3$, particularly preferably $1:\geqq 4$, in particular $1:\geqq 5$.

The reaction product obtained in step b) (i.e. the discharge from the reaction system) can be subjected to a work-up by customary methods known to those skilled in the art.

In a specific embodiment, the reaction product from step b) is divided into a first substream and a second substream after leaving the reaction system. This separation can be carried out by means of a customary separation device installed in the outlet tube. In the simplest case, this consists of a dividing wall of suitable geometry (e.g. Y-coupling) which is located in the outlet tube and from which the outlet stream is conveyed into two tubes, one for each of the substreams. In the case of fixed ratios of the substreams, these can be determined via the diameter of the branching tubes. To regulate the proportions of the two substreams, a slider device can be installed in one or both of the branching tubes. As an alternative, regulated offtake of the substreams can also be achieved by means of pumps.

In this embodiment, the proportion of the first substream to be worked up is preferably from 1 to 50% by weight, more preferably from 2 to 30% by weight, in particular from 5 to 20% by weight, based on the total weight of the discharge. The proportion of the second substream (circulation stream) is accordingly preferably from 50 to 99% by weight, particularly preferably from 70 to 98% by weight, in particular from 80 to 95% by weight, based on the total weight of the discharge.

The second substream is generally recirculated in chemically unchanged form to the reaction system. If desired, the temperature and/or the pressure can be set to the desired values before recirculation. The second substream can be fed into the reaction system together with one or both olefin starting materials or separately therefrom. The weight ratio of the second substream fed into the reaction system to the total olefin-comprising feed is preferably in the range from 1:1 to 50:1, particularly preferably from 2:1 to 30:1, in particular from 5:1 to 20:1.

The reaction product from step b) or the first substream of the discharge from the reaction system is subjected to a work-up by customary methods known to those skilled in the art. The discharge or the first substream is for this purpose subjected to a single-stage or multistage separation operation to give a stream comprising the major part of the codimerization product and a stream consisting essentially of unreacted olefin and possibly saturated hydrocarbon. Saturated hydrocarbons originate from, for example, the olefin-comprising feeds used for the oligomerization which can comprise these as components or, for example, to a small extent from a partial hydrogenation carried out to remove diolefins from the olefins used. Depending on the separation methods employed, further streams may be obtained, e.g. specific oligomer fractions or streams consisting essentially of saturated hydrocarbons.

A liquid stream is preferably taken off as discharge from the reaction system and is at least partly converted into the gas phase for the work-up. In the simplest embodiment, the liquid discharge from the reactor is for this purpose subjected to heating and/or depressurization, resulting in separation into a liquid phase and a gas phase. Here, the liquid phase generally comprises a product enriched in oligomeric reaction products while the gas phase is enriched in unreacted olefins and possibly saturated hydrocarbons. The liquid phase can then be subjected to a further separation, in general a thermal separation to give a fraction comprising the major part of the codimerization product and, if appropriate, further oligomer fractions. In a further embodiment, the direct separation of the reaction discharge (or the first substream) is effected by means of at least one thermal separation step, preferably a distillation step. Depressurization steps and/or thermal separation steps can be carried out in combination with one another in separate apparatuses or in a single apparatus, e.g. a "flash/strip column".

The stream consisting essentially of unreacted olefins and possibly saturated hydrocarbons which is obtained in the work-up of the reaction product from step b) can, if desired, be recirculated in part or in its entirety to the oligomerization reaction (step b)). To prevent accumulation of inert components, part or all of it can also be discharged from the system. Possible purposes of utilization are combustion, use for other chemical reactions or, for example, as feed in the cracking process for the renewed preparation of, for example, olefins which can be utilized in the process of the invention.

In a further suitable embodiment, a stream comprising saturated hydrocarbons and unreacted olefins which is obtained in the work-up of the reaction product from step b) is subjected to a further separation, e.g. by means of rectification, into an olefin-enriched fraction and an olefin-depleted fraction and the olefin-enriched fraction is at least partly recirculated to the oligomerization reaction (step b)). The olefin-depleted fraction can, as described above, be discharged from the process and, if appropriate, be utilized further.

Partial or total recirculation of the stream obtained after the codimers have been separated off in the work-up of the reaction product from step b) can, regardless of its alkene content, also be useful for controlling the desired codimer content.

The introduction of the stream consisting essentially of unreacted olefins and possibly saturated hydrocarbons which is obtained in the work-up of the reaction product can be effected separately or after prior mixing with one of the other feedstreams. Before introduction into the reactor, the temperature of each individual stream or stream mixture can be set by means of known devices, e.g. heat exchangers. If a reaction system which comprises a plurality of catalyst zones is used for the oligomerization reaction, individual streams or mixtures of these streams can be fed in at a plurality of points of the reaction system. If a reactor cascade comprising two or more reactors connected in series is used, it is possible to feed individual starting materials or the mixed starting material streams either entirely into the first reactor of the cascade or to divide them over the individual reactors of the cascade by means of a plurality of feed lines.

The invention further provides the olefin codimers obtainable by the above-described process.

The olefin codimers are preferably dimer mixtures as are obtained in the codimerization if at least one of the olefin starting materials comprises a mixture of at least two different olefins. Preference is given to olefin codimers which have been prepared using at least one industrially available olefin-comprising hydrocarbon mixture as olefin starting material. Particular preference is given to olefin codimers which have been prepared using a raffinate II as first olefin starting material and an olefin starting material obtainable by dimerization of a raffinate II as second olefin starting material. The second olefin starting material is then preferably an olefin starting material obtainable by dimerization of a raffinate II in the presence of a nickel-comprising oligomerization catalyst.

Preference is given to olefin codimers which have an ISO index in the range from 1.0 to 3.0, particularly preferably in the range from 1.5 to 2.5, in particular in the range from 1.7 to 2.3.

The ISO index can be determined NMR-spectroscopically from the area integrals of the $^1$H-NMR spectrum. This is explained as follows by way of example for $C_{12}$-olefin codimers (dodecenes):

The dodecenes are hydrogenated and in this way converted into alkanes having the empirical formula $C_{12}H_{26}$ (dodecanes). A $^1$H-NMR spectrum of the dodecanes is recorded and integrated blockwise. The resonances of the $CH_3$ protons are located in the range from 0.3 to 1.05 ppm. The resonances of the $CH_2$ and CH protons are located in the range from 1.05 to 2.8 ppm. The ratio of the integrals of the $CH_3$ block to the $CH_2$/CH block is formed. n-Dodecane has, for example, a ratio of $CH_3$ protons to $CH_2$/CH protons of 6:20 (x=0.3). Methylundecane has a ratio of $CH_3$ protons to $CH_2$/CH protons of 9:17 (x=0.53). Dimethyldecane has a ratio of $CH_3$ protons to $CH_2$/CH protons of 12:14 (x=0.86). The ISO index is calculated from the ratio x as follows:

$$\text{ISO index}=(20x-6)/(3x+3) \quad x=\text{ratio of } CH_3 \text{ protons to } CH_2/CH \text{ protons}$$

The olefin codimers are preferably mixtures comprising predominantly or exclusively alkenes having 12 carbon atoms. The olefin codimers then preferably comprise at least 70% by weight, particularly preferably at least 85% by weight, in particular at least 95% by weight, especially at least 95% by weight, based on the total olefin content, of alkenes having 12 carbon atoms.

Preference is given to olefin codimers whose $^1$H-NMR spectrum has an area integral of from 38 to 62%, preferably from 44 to 56%, particularly preferably from 47 to 53%, based on the total integral area, in the chemical shift range from 0.3 to 1.05 ppm, based on tetramethylsilane.

The invention further provides a process for preparing alcohols, which comprises
a) providing a first olefin starting material which consists essentially of $C_m$-olefins and providing a second olefin starting material which consists essentially of $C_n$-olefins, where n and m are, independently of one another, two different integers from 2 to 12,
b) feeding the first and second olefin starting materials into a first reaction zone and subjecting them to an oligomerization over a heterogeneous olefin oligomerization catalyst,
c) separating off a stream enriched in $C_{n+m}$-olefin codimers from the discharge from the first reaction zone,
d) feeding the stream enriched in $C_{n+m}$-olefin codimers into a second reaction zone and subjecting it to a reaction with carbon monoxide and hydrogen in the presence of a hydroformylation catalyst and
e) hydrogenating the hydroformylation product.

A preferred embodiment is a process for preparing alcohols having from 7 to 19 carbon atoms, which comprises
a) providing a first olefin starting material which consists essentially of $C_n$-olefins and providing a second olefin starting material which consists essentially of $C_{2n}$-olefins, where n is an integer from 2 to 6, b) feeding the first and second olefin starting materials into a first reaction zone and subjecting them to an oligomerization over a heterogeneous olefin oligomerization catalyst, c) separating off a stream enriched in $C_{3n}$-olefin codimers from the discharge from the first reaction zone, d) feeding the stream enriched in $C_{3n}$-olefin codimers into a second reaction zone and subjecting it to a reaction with carbon monoxide and hydrogen in the presence of a hydroformylation catalyst and e) hydrogenating the hydroformylation product.

As regards suitable and preferred embodiments of the process steps a) to c) and the intermediates obtained in these, reference is made to the totality of what has been said above.

Hydroformylation (Step d))

Suitable catalysts for the hydroformylation in step d) are known and generally comprise a salt or a complex of an element of transition group VIII of the Periodic Table. The metal of transition group VIII is preferably selected from among cobalt, ruthenium, iridium, rhodium, nickel, palladium and platinum. The process of the invention is preferably carried out using salts and in particular complexes of rhodium or of cobalt.

Suitable salts are, for example, the hydrides, halides, nitrates, sulfates, oxides, sulfides or the salts with alkylcarboxylic or arylcarboxylic acids or alkylsulfonic or arylsulfonic acids. Suitable complexes are, for example, the carbonyl compounds and carbonyl hydrides of the metals mentioned and also complexes with amines, amides, triarylphosphines, trialkylphosphines, tricycloalkylphosphines, allylarylphosphines, olefins or dienes as ligands. The ligands can also be used in polymeric or polymer-bonded form. Catalyst systems can also be prepared in situ from the abovementioned salts and the ligands mentioned.

Suitable alkyl radicals of the ligands are the above-described linear or branched $C_1$-$C_{15}$-alkyl radicals, in particular $C_1$-$C_5$-alkyl radicals. Cycloalkyl is preferably $C_3$-$C_{10}$-cycloalkyl, in particular cyclopentyl and cyclohexyl, which may optionally also be substituted by $C_1$-$C_4$-alkyl groups. Aryl is preferably phenyl (Ph) or naphthyl, which may optionally be substituted by 1, 2, 3 or 4 $C_1$-$C_4$-alkyl, $C_1$-$C_4$-alkoxy, e.g. methoxy, halogen, preferably chloride, or hydroxy groups, with the latter also being able, if appropriate, to be ethoxylated.

Suitable rhodium catalysts or catalyst precursors are rhodium(II) and rhodium(III) salts such as rhodium(III) chloride, rhodium(III) nitrate, rhodium(III) sulfate, potassium rhodium sulfate (rhodium alum), rhodium(II) or rhodium(III) carboxylate, preferably rhodium(II) and rhodium(III) acetate, rhodium(II) and rhodium(III) 2-ethylhexanoate, rhodium(III) oxide, salts of rhodic(III) acid and trisammonium hexachlororhodate(III).

Further suitable rhodium compounds are rhodium complexes of the general formula $RhX_mL^1L^2(L^3)_n$, where X is halide, preferably chloride or bromide, alkylcarboxylate or arylcarboxylate, acetylacetonate, arylsulfonate or alkylsulfonate, in particular phenylsulfonate and toluenesulfonate, hydride or the diphenyltriazine anion, where $L^1$, $L^2$, $L^3$ are each, independently of one another, CO, olefins, cycloolefins, preferably cyclooctadiene (COD), dibenzophosphole, benzonitrile, $PR_3$ or $R_2P$-A-$PR_2$, m is 1, 2 or 3 and n is 0, 1 or 2. The radicals R (which may be identical or different) are alkyl, cycloalkyl and aryl radicals, preferably phenyl, p-tolyl, m-tolyl, p-ethylphenyl, p-cumyl, p-t-butylphenyl, p-$C_1$-$C_4$-alkoxyphenyl, preferably p-anisyl, xylyl, mesityl, p-hydroxyphenyl which may, if appropriate, also be in ethoxylated form, isopropyl, $C_1$-$C_4$-alkoxy, cyclopentyl or cyclohexyl. A is 1,2-ethylene or 1,3-propylene. Preference is given to $L^1$, $L^2$ and $L^3$ each being, independently of one another, CO, COD, $P(phenyl)_3$, $P(i\text{-propyl})_3$, $P(anisyl)3$, $P(OC_2H_5)_3$, $P(cyclohexyl)_3$, dibenzophosphole or benzonitrile. X is preferably hydride, chloride, bromide, acetate, tosylate, acetylacetonate or the diphenyltriazine anion, in particular hydride, chloride or acetate.

Suitable cobalt compounds are, for example, cobalt(II) chloride, cobalt(II) sulfate, cobalt(II) nitrate, their amine or hydrate complexes, cobalt carboxylates such as cobalt acetate, cobalt ethylhexanoate, cobalt naphthenoate, and also the carbonyl complexes of cobalt, e.g. octacarbonyldicobalt, dodecacarbonyltetracobalt and hexadecacarbonyl-hexacobalt. Preference is given to using the cobalt carbonyl complexes and in particular octacarbonyldicobalt for the process of the invention.

The abovementioned compounds of rhodium and cobalt are known in principle and adequately described in the literature or they can be prepared by a person skilled in the art using methods analogous to those for the known compounds. This preparation can also be carried out in situ, with the catalytically active species also being able to be formed from the abovementioned compounds as catalyst precursors only under the hydroformylation conditions.

If a hydroformylation catalyst based on rhodium is used, it is generally used in an amount of from 1 to 150 ppm, preferably from 1 to 100 ppm. The reaction temperature for a hydroformylation catalyst based on rhodium is generally in the range from room temperature to 200° C., preferably from 50 to 170° C.

If a hydroformylation catalyst based on cobalt is used, it is generally used in an amount of from 0.0001 to 1.0% by weight, based on the amount of the olefins to be hydroformylated. The reaction temperature for a hydroformylation catalyst based on cobalt is generally in the range from about 80 to 250° C., preferably from 100 to 220° C., particularly preferably from 150 to 200° C.

The reaction can be carried out at an elevated pressure of from about 10 to 650 bar.

The molar ratio of $H_2$:CO is generally from about 1:5 to about 5:1 and preferably about 1:1.

Step d) is preferably carried out using a hydroformylation catalyst which is capable of hydroformylating linear monoolefins to give a high proportion of n-aldehydes.

Hydroformylation catalysts having a high n selectivity are known from the prior art. They include complexes of metals of transition group VIII with bisphosphite and polyphosphite ligands, as are described in U.S. Pat. No. 4,668,651, U.S. Pat. No. 4,748,261, U.S. Pat. No. 4,769,498 and U.S. Pat. No. 4,885,401. They also include complexes of metals of transition group VIII with bidentate phosphorus-comprising ligands which have a 1,1'-biphenylylene bridging group or a 1,1'-binaphthylylene bridging group, as are described in WO 98/19985 and EP-A-0 937 022. The ligands mentioned are hereby fully incorporated by reference.

The crude aldehydes or aldehyde/alcohol mixtures obtained in the hydroformylation can, if desired, be isolated and, if appropriate, purified by customary methods known to those skilled in the art, prior to the hydrogenation.

Hydrogenation (Step e))

To carry out the hydrogenation, the reaction mixtures obtained in the hydroformylation are reacted with hydrogen in the presence of a hydrogenation catalyst.

Suitable hydrogenation catalysts are in general transition metals such as Cr, Mo, W, Fe, Rh, Co, Ni, Pd, Pt, Ru, etc., or mixtures thereof which can be applied to supports such as activated carbon, aluminum oxide, kieselguhr, etc., to increase the activity and stability. To increase the catalytic activity, Fe, Co and preferably Ni can also be used in the form of the Raney catalysts as metal sponge having a very high surface area. A Co/Mo catalyst is preferably used for preparing the surfactant alcohols according to the invention. The hydrogenation of the oxo aldehydes is, depending on the activity of the catalyst, preferably carried out at elevated temperatures and superatmospheric pressure. The hydrogenation temperature is preferably from about 80 to 250° C., and the pressure is preferably from about 50 to 350 bar.

The alcohol mixture according to the invention, especially a $C_{13}$-alcohol mixture, can be isolated in pure form from the reaction mixture obtained after the hydrogenation by means of customary purification methods known to those skilled in the art, in particular by fractional distillation.

The invention also provides a functionalized alcohol mixture which is obtained by subjecting an above-described alcohol mixture to
(i) alkoxylation,
(ii) glycosidization,
(iii) sulfation,
(iv) phosphation,
(v) alkoxylation and subsequent sulfation or
(vi) alkoxylation and subsequent phosphation.

The alcohol mixture is especially a functionalized $C_{13}$-alcohol mixture.

The alkoxylation of the alcohol mixtures is effected by reaction with at least one alkylene oxide. The alkylene oxides are preferably selected from among compounds of the general formula I

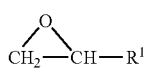
(I)

where
$R^1$ is hydrogen or a straight-chain or branched $C_1$-$C_{16}$-alkyl radical,
and mixtures thereof.

The radical $R^1$ in the formula I is preferably a straight-chain or branched $C_1$-$C_8$-alkyl radical, in particular $C_1$-$C_4$-alkyl radical.

The alkylene oxides are preferably selected from among ethylene oxide, propylene oxide, butylene oxide and mixtures thereof.

The reaction of the alcohol mixtures with the alkylene oxide(s) is carried out using customary methods known to those skilled in the art and in apparatuses customary for this purpose.

The mean chain length of the polyether chains of the alcohol mixtures which have been functionalized in this way can be determined by the molar ratio of alcohol to alkylene oxide. Preference is given to preparing alkoxylated alcohol mixtures having from about 1 to 200, preferably from about 1 to 50, in particular from 1 to 10, alkylene oxide units.

The alcohol mixtures can, if desired, be reacted with only one alkylene oxide or with two or more different alkylene oxides. In the reaction of the alcohol mixtures with a mixture of two or more alkylene oxides, the resulting alkoxylates comprise the alkylene oxide units in an essentially random distribution. If the alkylene oxides are used separately in succession, the resulting alkoxylates comprise the alkylene oxide units polymerized in the form of blocks corresponding to the order of addition.

The alkoxylation can be catalyzed by strong bases such as alkali metal hydroxides and alkaline earth metal hydroxides, Brönsted acids or Lewis acids such as $AlCl_3$, $BF_3$, etc.

The alkoxylation is preferably carried out at temperatures in the range from about 80 to 250° C., preferably from about 100 to 220° C. The pressure is preferably in the range from ambient pressure to 600 bar. If desired, the alkylene oxide can comprise an addition of inert gas, e.g. from about 5 to 60%.

The functionalized alcohol mixtures obtained by alkoxylation display a very good surface activity and can advantageously be used as nonionic surfactants in many applications, e.g. as surfactant, dispersant, paper auxiliary, dirt-dissolving agent, corrosion inhibitor, auxiliary for dispersions or encrustation inhibitor.

The glycosidization of the alcohol mixtures is effected by single, double or multiple reaction of the alcohol mixtures according to the invention with monosaccharides, disaccharides or polysaccharides. The reaction is carried out by customary methods known to those skilled in the art. These include, firstly, acid-catalyzed reaction with withdrawal of water. Suitable acids are, for example, mineral acids such as HCl and $H_2SO_4$. Here, oligosaccharides having a random chain length distribution are generally obtained. The average degree of oligomerization is preferably from 1 to 3 saccharide radicals. According to a further suitable process, the saccharide can firstly be acetalized by reaction with a low molecular weight $C_1$-$C_8$-alkanol such as ethanol, propanol or butanol. The acetalization is preferably acid-catalyzed. The resulting glycoside with the low molecular weight alcohol can subsequently be reacted with an alcohol mixture according to the invention to form the corresponding glycosides. Aqueous saccharide solutions are generally also suitable for this reaction. In a further suitable process, the saccharide can firstly be converted into the corresponding O-acetylhalosaccharide by reaction with a hydrogen halide and subsequently be glycosidized by means of an alcohol mixture according to the invention in the presence of acid-binding compounds.

The glycosidization is preferably carried out using monosaccharides. In particular, use is made of hexoses such as glucose, fructose, galactose, mannose etc., and pentoses such as arabinose, xylose, ribose, etc. Particular preference is given to using glucose. The saccharides can be used individually or in the form of mixtures. In the case of saccharide mixtures, glycosides having randomly distributed sugar radicals generally result. In the case of addition of a plurality of saccharide units onto an alcoholic hydroxide group, polyglycosides of the alcohol mixtures according to the invention result. For polyglycosidization, too, a plurality of saccharides can be used in succession or as a mixture, so that the resulting functionalized alcohol mixtures comprise the saccharides incorporated in the form of blocks or randomly distributed. Depending on the reaction conditions, in particular the reaction temperature, furanose or pyranose structures can result.

Suitable processes and reaction conditions for glycosidization are described, for example, in Ullmann's Encyclopedia of Industrial Chemistry, 5th edition, vol. A25 (1994), p. 792-793, and the documents cited therein.

The functionalized alcohol mixtures obtained by glycosidization display a very good surface activity and can advantageously be used as nonionic surfactants in many applications.

The sulfation or phosphation of the above-described alcohol mixtures or alkoxylated alcohol mixtures is effected by reaction with sulfuric acid or sulfuric acid derivatives to form acid alkyl sulfates or alkyl ether sulfates or by reaction with phosphoric acid or phosphoric acid derivatives to form acid alkyl phosphates or alkyl ether phosphates.

Suitable processes for the sulfation of alcohols are the customary processes which are known to those skilled in the art, as are described, for example, in U.S. Pat. No. 3,462,525, U.S. Pat. No. 3,420,875 or U.S. Pat. No. 3,524,864, which are hereby fully incorporated by reference. Suitable sulfation processes are also described in Ullmann's Encyclopedia of Industrial Chemistry, 5th edition, vol. A25 (1994), pp. 779-783, and the references cited therein.

If sulfuric acid is used for the sulfation of the alcohol mixtures according to the invention, it preferably has a concentration of from 75 to 100% by weight, in particular from 85 to 98% by weight. Such sulfuric acid is obtainable under the names concentrated sulfuric acid and monohydrate.

If desired, a solution or diluent can be used for sulfation by means of sulfuric acid. Suitable solvents are, for example, those which form an azeotrope with water, e.g. toluene.

In a suitable embodiment of the preparation of sulfated alcohol mixtures, the alcohol mixture is placed in a reaction vessel and the sulfating agent is added while mixing continually. To achieve very complete esterification of the alcohol mixture, the molar ratio of alkanol to sulfating agent is preferably from about 1:1 to 1:1.5, in particular from 1:1 to 1:1.2. If desired, the sulfating agent can also be used in a molar deficit, e.g. in the sulfation of alkoxylated alcohol mixtures, when mixtures of nonionic and anionic surface-active compounds are to be prepared. The sulfation is preferably carried out at a temperature in the range from ambient temperature to 80° C., in particular from 40 to 75° C.

Further suitable sulfating agents are, for example, sulfur trioxide, sulfur trioxide complexes, solutions of sulfur trioxide in sulfuric acid (oleum), chlorosulfonic acid, sufuryl chloride, amidosulfonic acid, etc. When sulfur trioxide is used as sulfating agent, the reaction can advantageously be carried out in a falling film evaporator, preferably in countercurrent. The reaction can be carried out batchwise or continuously.

The reaction mixtures formed in the sulfation are worked up by customary methods known to those skilled in the art. These include, for example, neutralization, removal of any solvents used, etc.

The phosphation of the above-described alcohol mixtures and alkoxylated alcohol mixtures is generally carried out in a manner analogous to sulfation.

Suitable processes for the phosphation of alcohols are the customary processes known to those skilled in the art, as are described, for example, in Synthesis 1985, pp. 449-488, which is hereby fully incorporated by reference.

Suitable phosphating agents are, for example, phosphoric acid, polyphosphoric acid, phosphorus pentoxide, $POCl_3$, etc. When $POCl_3$ is used, the remaining acid chloride functions are hydrolyzed after the esterification.

The invention further provides for the use of the functionalized alcohol mixtures as surfactants, dispersants, paper auxiliaries, dirt-dissolving agents, corrosion inhibitors, auxiliaries for dispersions, encrustation inhibitors.

The invention is illustrated by the following, nonlimiting examples.

EXAMPLES

Example 1

According to the Invention

An oil-heated double-walled tube reactor (d (internal)=6 mm, l=70 cm) was filled with 8 ml of crushed catalyst (1 to 1.6 mm diameter). The catalyst used was an H-β-zeolite shaped using aluminum oxide (boehmite) as binder (molar ratio of $SiO_2$:$Al_2O_3$=24). Activation was carried out at 250° C. in a stream of nitrogen for 18 hours. The reaction was carried out at a pressure of 25 bar. 12 g/h of a mixture of 64% by weight of $C_8$-olefin and 36% by weight of $C_4$-Olefin were metered in as feed. The $C_8$-olefin having an ISO index of 1.08 originated from a butene dimerization and comprised 3-methylheptene as main component. The composition of the $C_4$-olefin was as follows: 1-butene (37%), 2-butene (42%), isobutene (2%), isobutane (3%), n-butane (16%). In addition to the feed stream, a recycle stream of 76 g/h was passed through the reactor.

The experiment was evaluated by means of on-line gas chromatography (GC) using a flame ionization detector, with the composition of feed and reactor discharge being determined. Table 1 shows the difference of the GC-% by area values (reactor discharge–feed) as a function of the time of operation and the temperature. It can clearly be seen that both butenes and octenes are reacted.

The discharges were collected and distilled. The $C_{12}$-comprising fraction was hydrogenated and the ISO index was subsequently determined by $^1$H-NMR spectroscopy. It was 2.1.

The $^1$H-NMR spectrum of the $C_{12}$-olefin-comprising fraction has an area integral of 51% based on the total integral area in the region of a chemical shift δ from 0.3 to 1.05 ppm.

TABLE 1

| Time of operation [h] | Temperature [° C.] | $C_4$ [Δ % by area] | $C_8$ [Δ % by area] | $C_{12}$ [Δ % by area] | $C_{16}$ [Δ % by area] |
|---|---|---|---|---|---|
| 100 | 60 | −3.87 | −4.29 | 6.25 | 1.98 |
| 160 | 80 | −5.89 | −5.73 | 8.59 | 3.01 |

Comparative Example

This was carried out in a manner analogous to example 1. 8 ml of a supported $NiO/SiO_2$ catalyst were used as catalyst. Table 2 shows the difference of the GC-% by area values (reactor discharge–feed) as a function of the time of operation and the temperature. In contrast to example 1, only the butenes are reacted.

TABLE 2

| Time of operation [h] | Temperature [° C.] | $C_4$ [Δ % by area] | $C_8$ [Δ % by area] | $C_{12}$ [Δ % by area] | $C_{16}$ [Δ % by area] |
|---|---|---|---|---|---|
| 24 | 61 | −17.95 | 8.47 | 7.27 | 2.12 |
| 61 | 80 | −19.80 | 9.89 | 7.91 | 1.90 |

The invention claimed is:

1. A process for codimerizing olefins, which comprises:
    a) providing a first olefin starting material which consists essentially of $C_n$-olefins and providing a second olefin starting material which consists essentially of $C_m$-olefins, wherein n and m are, independently of one another, two different integers from 2 to 12, wherein the second olefin starting material has a degree of branching of the olefins, determined as the ISO index, in the range from 0 to 1.8 and is obtained by dimerization of a raffinate II in the presence of a nickel-comprising oligomerization catalyst; and
    b) reacting the first and second olefin starting materials over a heterogeneous olefin oligomerization catalyst, the heterogeneous olefin oligomerization catalyst having a nickel content of not more than 1% by weight, based on the total weight of the catalyst.

2. The process according to claim 1, wherein, in step a), a first olefin starting material which consists essentially of $C_n$-olefins is provided and a second olefin starting material which consists essentially of $C_2$-olefins, where n is an integer from 2 to 6, is provided.

3. The process according to claim 2, wherein n is 4.

4. The process according to claim 1, wherein the first olefin starting material has a proportion of branched olefins of not more than 20% by weight, particularly preferably not more than 10% by weight, in particular not more than 5% by weight, especially not more than 3% by weight, based on the total olefin content.

5. The process according to claim 1, wherein an industrially available olefin-comprising hydrocarbon mixture from a cracking process is used as first olefin starting material.

6. The process according to claim 5, wherein a raffinate II is used as first olefin starting material.

7. The process according to claim 1, wherein the second olefin starting material has a degree of branching of the olefins, determined as the ISO index, in the range from 0.5 to 1.5, in particular from 0.8 to 1.3.

8. The process according to claim 1, wherein the second olefin starting material is obtained by the Dimersol process or by the Octol process.

9. The process according to claim 1, wherein the reaction of the olefin starting materials in step b) is carried out continuously.

10. The process according to claim 1, wherein the reaction product from step b) is separated into a first substream and a second substream, the first substream is subjected to a workup to give a fraction comprising essentially the codimerization product and the second substream is recirculated to step a).

11. The process according to claim 1, wherein the molar ratio of $C_m$-olefins to $C_n$-olefins, in particular the molar ratio of $C_{2n}$-olefins to $C_n$-olefins, based on the olefins fed in step b), is in the range from 0.25:1 to 4:1, preferably in the range from 0.5:1 to 3:1.

12. The process according to claim 1, wherein the first olefin starting material and the second olefin starting material are reacted over a heterogeneous olefin oligomerization catalyst based on a sheet and/or framework silicate in step b).

13. The process according to claim 12, wherein the sheet and/or framework silicates of the oligomerization catalyst used in step b) have a proportion of crystalline material of at least 50% by weight.

14. The process according to claim 12, wherein the oligomerization catalyst used in step b) comprises at least one porous silicate having a mean pore diameter of at least 0.5 nm.

15. The process according to claim 12, wherein the oligomerization catalyst used in step b) comprises at least one zeolite or consists of a zeolite.

16. A process for preparing alcohols, which comprises:
a) providing a first olefin starting material which consists essentially of $C_m$-olefins and providing a second olefin starting material which consists essentially of $C_n$-olefins, wherein n and m are, independently of one another, two different integers from 2 to 12, and wherein the second olefin is obtained by dimerization of a raffinate II in the presence of a nickel-comprising oligomerization catalyst;
b) feeding the first and second olefin starting materials into a first reaction zone and subjecting them to an oligomerization over a heterogeneous olefin oligomerization catalyst, the heterogeneous olefin oligomerization catalyst having a nickel content of not more than 1% by weight, based on the total weight of the catalyst;
c) separating off a stream enriched in $C_{n+m}$-olefin codimers from the discharge from the first reaction zone;
d) feeding the stream enriched in $C_{n+m}$-olefin codimers into a second reaction zone and subjecting it to a reaction with carbon monoxide and hydrogen in the presence of a hydroformylation catalyst; and
e) hydrogenating the hydroformylation product.

17. A process for preparing alcohols having from 7 to 19 carbon atoms, which comprises:
a) providing a first olefin starting material which consists essentially of $C_n$-olefins and providing a second olefin starting material which consists essentially of $C_{2n}$-olefins, wherein n is an integer from 2 to 6, and wherein the second olefin is obtained by dimerization of a raffinate II in the presence of a nickel-comprising oligomerization catalyst;
b) feeding the first and second olefin starting materials into a first reaction zone and subjecting them to an oligomerization over a heterogeneous olefin oligomerization catalyst, the heterogeneous olefin oligomerization catalyst having a nickel content of not more than 1% by weight, based on the total weight of the catalyst;
c) separating off a stream enriched in $C_{3n}$-olefin codimers from the discharge from the first reaction zone;
d) feeding the stream enriched in $C_{3n}$-olefin codimers into a second reaction zone and subjecting it to a reaction with carbon monoxide and hydrogen in the presence of a hydroformylation catalyst; and
e) hydrogenating the hydroformylation product.

* * * * *